(12) United States Patent  (10) Patent No.: US 8,252,298 B2
Maderazzo et al.  (45) Date of Patent: Aug. 28, 2012

(54) COLOR COSMETIC

(75) Inventors: Kimber Maderazzo, Pacific Palisades, CA (US); Nathalie Schlemer, Culver City, CA (US); Gabriel E. Uzunian, Rye, NY (US); Betty Aucar, Ossining, NY (US)

(73) Assignee: Guthy-Ranker LLC et al., Santa Monica, CA (US)

( * ) Notice: Subject to any disclaimer, the term of this patent is extended or adjusted under 35 U.S.C. 154(b) by 447 days.

(21) Appl. No.: 12/701,394

(22) Filed: Feb. 5, 2010

(65) Prior Publication Data

US 2010/0209464 A1 Aug. 19, 2010

Related U.S. Application Data

(60) Provisional application No. 61/152,587, filed on Feb. 13, 2009.

(51) Int. Cl.
*A61K 8/02* (2006.01)
*A61K 8/18* (2006.01)
*A61Q 1/02* (2006.01)
*A61Q 1/12* (2006.01)
*A61Q 17/04* (2006.01)

(52) U.S. Cl. ......... 424/401; 424/63; 424/59; 424/70.13; 424/49; 424/64; 424/61; 424/70.7

(58) Field of Classification Search .................. None
See application file for complete search history.

(56) References Cited

U.S. PATENT DOCUMENTS

| 4,623,396 | A | 11/1986 | Kimura et al. |
|---|---|---|---|
| 5,116,664 | A | 5/1992 | Kimura et al. |
| 5,690,916 | A | 11/1997 | Kimura et al. |
| 6,306,409 | B1 | 10/2001 | Ogawa et al. |
| 2007/0140984 | A1* | 6/2007 | Kusano et al. .......... 424/49 |
| 2008/0110372 | A1 | 5/2008 | Hollman et al. |
| 2008/0112909 | A1 | 5/2008 | Faler et al. |
| 2008/0115694 | A1 | 5/2008 | Hollman et al. |
| 2008/0118452 | A1 | 5/2008 | Hollman et al. |
| 2008/0124575 | A1 | 5/2008 | Hollman et al. |

OTHER PUBLICATIONS

Uzunian et al.; "The Impact of Skin Tone on the Color Generated by Effect Pigments," May 11, 2001, Society of Cosmetic Chemists Annual Scientifc Seminar, New Orleans LA, Sheets.
Maile, et al.; "Effect Pigments—Past, Present, and Future," Progress in Organic Coatings, 54, 2005, pp. 150-163.
Uzunian et al.; Presentation Document; "Frontiers in Effect Pigment Technology—The Borosilicate Platform," Mar. 9-11, 2004, Personal Care Ingredients Asia in China, Sheets.

* cited by examiner

*Primary Examiner* — Ernst Arnold
*Assistant Examiner* — Hong Yu
(74) *Attorney, Agent, or Firm* — Cislo & Thomas, LLP

(57) ABSTRACT

A foundation having a shade which covers a wide spectrum of different skin tones and undertones, comprises red and gold interference pigments, which provide a formula that is adaptable to both red and yellow skin undertones. The composition virtually eliminates the risk of application of the wrong foundation color, and provides enhanced color and textural effects, and superior optical performance.

10 Claims, 1 Drawing Sheet

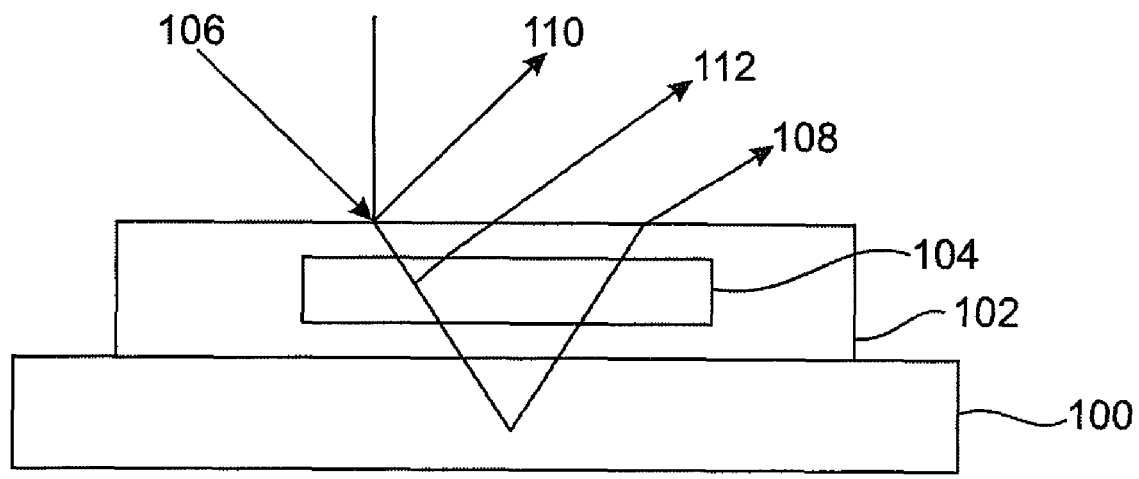

COLOR COSMETIC

CROSS-REFERENCE TO RELATED APPLICATIONS

This application is related to, and claims priority through earlier filed Provisional Patent Application Ser. No. 61/152,587, filed on Feb. 13, 2009, which is related to, and claims priority through earlier filed International Patent Application Serial No. US2008/002148, filed on Feb. 19, 2008, which is related to and claims priority through earlier filed U.S. Continuation-in-Part application Ser. No. 11/899,773, filed on Sep. 7, 2007, which is related to, and claims priority through earlier filed U.S. application Ser. No. 11/655,420, filed Jan. 19, 2007, all the subject matter of which are herein incorporated by this reference thereto in their entirety for all purposes.

FIELD OF THE INVENTION

The present invention relates to cosmetic compositions, and more particularly to color cosmetics such as foundations, concealers, cover-ups, and the like.

DESCRIPTION OF THE RELATED ART

Color cosmetics formulated to mask, enhance or modify the user's skin tone typically come in a variety of shades, as there is great variation in individual skin tones and undertones, which vary from light beige to dark brown.

Effect or pearlescent pigments have been widely used in color cosmetic and personal care applications, and various studies have been carried out to measure and characterize effect pigments, including taking into account the affect of skin tones on color appearance. (See, for example, G. Uzunian and O. Dueva, "The Impact of Skin Tone on the Color Generated by Effect Pigments", presented on May 11, 2001 at Society of Cosmetic Chemists Annual Scientific Seminar in New Orleans, La., USA.)

Additionally, incorporating effect or pearlescent pigments in such color cosmetic and personal care formulations enhance or modify the user's skin tone and can provide contrasting effects.

However, as differences in the color appearance of most commercial cosmetics and users' skin tones are subtle, finding a shade which truly complements and improves the user's appearance is an uncertain process. The process is further complicated given that the color expression can be affected by the user's own skin tone. This may be particularly true for lighter coverage cosmetics and cosmetics including effect pigments, which are relatively transparent; where, most often, the resulting color on the skin is not the same as the color that appears as the mass tone.

As shown in FIG. 1, incident light 106 reflected from the cosmetic combines with the light reflected from the skin. When observing a skin surface 100 applied with cosmetic products 102, the visual appearance effect is a combination of skin color (reflected light 108) and cosmetic product (reflected light 110) containing effect pigments 104 (reflected light 112). Thus, the resulting color on the skin is often not the same as the color that appears as the mass tone.

Additionally, traditional makeup foundations are designed to impart an even application close to the user's skin tone. However consumers also often expect the enhanced coloristic effects that cosmetic products impart.

Given the above, there is a need for color cosmetics which optimally match and beautify a user's skin tone, and which take away the uncertainty of matching the cosmetic shade to the user's skin color.

SUMMARY

The present invention provides a make up formulation particularly suitable for application to the face, and for use as a foundation, cover up, concealer, finishing powder, and the like, comprising red and gold interference pigments, which has a shade that covers a wide spectrum of different skin tones and undertones, virtually eliminating the risk of application of the wrong foundation color. The formulation has superior tone stability and adaptability, providing enhanced color and textural effects, and superior optical performance.

OBJECTS OF THE INVENTION

It is an object of the present invention to provide a cosmetic suitable for use as a foundation, cover up, concealer, finishing powder, and the like, which is adaptable to a wide range of skin tones and undertones.

It is a further object to provide such a formulation containing effect pigments which provide enhanced color and textural effects.

It is another object of the present invention to provide such a cosmetic and cosmetic method which greatly reduces the risk of applying the wrong color.

The foregoing objects are some of but a few of the goals sought to be attained by the present invention and are set forth for the purposes of example only and not those of limitation.

BRIEF DESCRIPTION OF THE DRAWINGS

FIG. 1 is a diagram showing the optical effect of a cosmetic formulation containing effect pigments on the skin.

DETAILED DESCRIPTION OF THE PREFERRED EMBODIMENT

The detailed description set forth below is intended as a description of exemplary embodiments and is not intended to represent the only forms in which the exemplary embodiments may be constructed and/or utilized. The description sets forth the functions and the sequence of steps for formulating the exemplary embodiments. However, it is to be understood that the same or equivalent functions and sequences may be accomplished by different exemplary methods are also intended to be encompassed within the spirit and scope of the invention, and within the scope and judgment of the skilled person.

The present invention provides a skin coverage cosmetic and method comprising the application of a composition including a combination of gold/yellow and red special effect pigments which matches a wide spectrum of different skin tones and undertones, virtually eliminating the risk of application of the wrong foundation color. (It is noted that the terms "gold" and "yellow" are used interchangeably herein.)

The inventive and unexpected shade adapting capabilities of the present formulation was discovered by the inventors as a result of research on the complex interplay between special effects mineral pigment technology and skin tones. This research showed that a formulation containing the red and yellow interference pigments is capable of accommodating at least 6 and up to 24 different skin tones, outside the range of the apparent mass tone of the formulation.

The product is preferably formulated as a loose or pressed powder, and can further be formulated as a foundation, concealer or cover up, finishing powder, and the like, in a suitable cosmetic medium.

According to a preferred embodiment, the composition comprises gold and red special effect pigments, in combination with unfermented green rooibos (aspalathus linearis leaf) extract, boron nitride powder, zinc oxide, bisabolol, lauroyl lysine coated mica, bismuth oxychloride, and other colorants and visual effect agents including mica and iron oxides. This combination provides a mineral foundation cosmetic which is adaptable to both red and yellow skin tones and undertones, or a combination thereof, and is further suitable for green or bronze (olive skin) and beige or brown (neutral) undertones, providing both brightening effects and color shifts, with superior tone stability and adaptability.

Special effect, or pearlescent pigments have platelets which produce a pearlescent effect by specular reflection of light from the many surfaces of the platelets with parallel orientation at various depths within the coating film. (See Maile F. J., Pfaff G., Reynders P. Effect Pigments-Past, Present, and Future. *Progress in Organic Coatings* 54, 2005, pp. 150-163.) Light striking the platelets is partially reflected and partially transmitted through the platelets. A pearly luster effect is produced by the dependence of reflection on viewing angle, and the sense of depth is created by reflection from many layers. The platelets must be extremely smooth to maximize reflected light as opposed to regular, non-special effect colorants which typically have surface roughness that diminishes the lustrous effect.

The gold mineral and red mineral special effect pigments used for the formulation of the present invention are preferably titanium dioxide coated particles with a refractive index range generally between 2.4 to 2.8, and a d50 particle size of between approximately 6 μm to 300 nm. The thin films of titanium dioxide on mica produce a light interference effect that manifests itself as iridescent colors. Though mica based pigments are preferred, pigment with other substrates, such as borosilicate, alumina, silica, synthetic fluorphlogopite (synthetic mica), and bismuth oxychloride may also be used.

Although the interference layer of the pigments preferably comprise a metal oxide, such as iron or titanium, other high index of refraction materials that can be formed as thin layers, e.g., bismuth oxychloride, are also within the scope of the invention. Additionally, though the interference pigments are typically bilayered, special effect pigments made of an optically homogeneous material or substrate-free pigments which produce an interference effect (e.g. single layer, substrate free TiO2) are also within the contemplated scope of the invention.

The preferred gold mineral special effect pigment is Flamenco® Satin Gold 260 M, (mean particle diameter 7.9 μm, optical thickness of titanium dioxide 190 nm) which is an off white, free flowing powder with a pale gold reflection color composed of pigment type platelets of mineral mica, titanium dioxide and a small amount of iron oxide. This pigment counteracts ruddy skin tones associated with skin that burns easily, but also that easily becomes flushed or pink cheeked.

A preferred red mineral special effect pigment is Flamenco® Satin Red 460 M, (mean particle diameter of 6.8 μm, optical thickness of titanium dioxide 260 nm), which is an off-white, free flowing powder with a pale red reflection color composed of pigment type platelets of mineral mica, titanium dioxide, and a small amount of iron oxide. This pigment counteracts olive and yellow skin undertones which respond poorly to yellowish foundation and concealer and which can be slightly gray or ashy.

Preferably, each of the special effect pigments is present in the formulation in a range of about 0.5% to 15% by weight, more preferably between 1 and 10%, and most preferably between 2 and 7% depending on the type of shade. Most preferably, each pigment is present at between 2 and 4% for dark shades, and between 5 and 7% for medium to light shades. Additionally, the pigments are most preferably present at a gold to red pigment ratio of between about 1:2 and 2:1, and most preferably at about 1:1. This combination is adapted to pick up and reflect skin tone, and perfect the skin's appearance by reflecting the light and mimicking the skin tone.

Other examples of suitable pigments include, but are not limited to, Flamenco® Gold 220C and Flamenco® Red 420C, Flamenco® Super Gold 230Z and Flamenco® Super Red 430Z, Flamenco® Summit Gold Y30D and Flamenco® Summit Red R30D, Flamenco® Sparkle Gold 220J and Flamenco® Sparkle red 420J, Reflecks Dimensions® Shimmering Gold G230Z and Reflecks Dimensions® Shimmering Red G430Z, Reflecks Dimensions® Luminous Gold G230M and Reflecks Dimensions® Luminous Red G430M, Reflecks Dimensions® Sparkling Gold G230D and Reflecks Dimensions® Sparkling Red G430D.

Other key ingredients in the formulation include unfermented green rooibos (aspalathus linearis leaf) extract, boron nitride powder, zinc oxide, bisabolol, and lauroyl lysine coated mica, and bismuth oxychloride. The formulation may also contain other colorants and visual effect agents besides the special effect pigments, such as mica and iron oxides.

The rooibos plant extract has a very unique and potent flavonoid called aspalathin, which exhibits antioxidant, anti-inflammatory and free radical scavenging properties. This ingredient is present in the formulation at a range of approximately 0.01% to 2% by weight, and more preferably at approximately 0.1%.

The boron nitride powder, which is a slip agent, has light diffusing properties to blur imperfections, and a silky smooth feel. The tactile benefits of boron nitride result from the hexagonal planar crystal structure of boron nitride powder. This crystalline structure also contributes to its better adhesion, absorption, soft focus, and cooling effects. This ingredient is present in the formulation at a range of approximately 0.1% to 10% by weight, and more preferably at approximately 1%.

Zinc oxide, which is preferably mirconized, is used as a sunscreen agent, and is preferably present at a range of approximately 9-15% by weight, the preferred amount being approximately 12%.

Bisabolol which is a plant derived skin soothing agent, is preferably present at a concentration range of approximately at least 0.05% by weight, and more preferably at approximately 0.1%. Though bisabolol is a preferred skin soothing agent, alternative natural soothing or anti-irritation ingredients may be used including various botanical extracts, antioxidants and minerals.

Mica which is coated or surface treated with lauroyl lysine, is generally used in the formulation for visual and tactile effect, and is preferably present at a concentration range of approximately 15 to 30%, and more preferably at approximately 20%. Alternative surface treatments, such as titanium oxide or iron oxide may be used; however, lauroyl lysine is preferred for its tactile feel and texture.

Bismuth oxychloride which is generally used in the formulation as a colorant and skin adhesion agent can be present at a concentration of between 5 to 30% by weight.

The formulation preferably contains other colorants and visual effect agents besides the special effect pigments including mica and iron oxides, for providing a shade which is more ideally suited to a particular skin color range.

The following are examples of formulations prepared in accordance with a preferred embodiment of the invention. Each shade is formulated to cover at least 6 and up to about 24 different skin tones, including tones outside the range of the apparent shade or mass tone of the formulation. It is noted that the lighter shade of Examples 2-4 appear to cover a larger range and variety of skin tones than the darker shade of Example 1. These formulations include special effect red and gold pigments, and regular, non-special effect colorants comprising iron oxides. The formulations may be applied for light to heavy coverage, depending on the user's preferences.

Example 1

The tables below provides a list of ingredients for a loose powder mineral foundation having an SPF of 15, and a "Chocolate" shade, suitable for very dark skin tones.

| Trade Name (*phase A or B indicated in brackets) | INCI Name | % Wt | % Comp Breakdown | Function | Manufacturer |
| --- | --- | --- | --- | --- | --- |
| (A) Z-Cote | Zinc Oxide | 12.0000% | 100.00% | Sunscreen | BASF |
| (A) Unipure Red LC381 | Iron Oxides (CL 77491) | 6.200% | 100.00% | Colorant | LCW |
| (A) Unipure Yellow LC181 | Iron Oxides (CL 77492) | 9.5200% | 100.00% | Colorant | LCW |
| (A) Unipure Black LC989 | Iron Oxides (CL 77499) | 3.3400% | 100.00% | Colorant | LCW |
| (A) Boron Nitride Powder C6058 | Boron Nitride | 1.0000% | 100.00% | Slip Agent | GE Advanced Ceramics |
| (A) Bisabolol Nat. | Bisabolol | 0.1000% | 100.00% | Skin Soothing Agent | BASF |
| (A) Unfermented Green Rooibos Extract | Aspalathus Linearis Leaf Extract | 0.1000% | 100.00% | Antioxidant | Jarchem |
| (B) Mearlmica SVA | Mica (and) Lauroyl Lysine | 20.0000% | 95.50%, 4.50% | Visual Effect | BASF |
| (B) Mearlmica MMCF | Mica | 30.7400% | 100.00% | Visual Effect | BASF |
| (B) Pearl-Glo UVR | Bismuth Oxychloride CL77163 | 9.0000% | 100.00% | Skin Adhesion | BASF |
| (B) Flamenco Satin Gold 260M | Mica (and) Titanium Dioxide (and) Iron Oxides (CL77491) | 3.0000% | 36.00%, 62.00%, 2.00% | Colorant | BASF |
| (B) Flamenco Satin Red 460M | Mica (and) Titanium Dioxide (and) Iron Oxides (CL77491) | 3.0000% | 30.00%, 68.00%, 2.00% | Colorant | BASF |
| (B) Mearlmica MMCF | Mica | 2.0000% | 100.00% | Visual Effect | BASF |

Example 2

The table below provides a list of ingredients for a loose powder mineral foundation having an SPF of 15, and an "Almond" or "tan" shade.

| Trade Name (*phase A or B indicated in brackets) | INCI Name | % Wt | % Comp Breakdown | Function | Manufacturer |
| --- | --- | --- | --- | --- | --- |
| (A) Z-Cote | Zinc Oxide | 12.0000% | 100.00% | Sunscreen | BASF |
| (A) Atlas White Titanium Dioxide | Titanium Dioxide | 10.0000% | 100.00% | Colorant | LCW |
| (A) Unipure Red LC381 | Iron Oxides (CL 77491) | 1.9000% | 100.00% | Colorant | LCW |
| (A) Unipure Yellow LC181 | Iron Oxides (CL 77492) | 9.5000% | 100.00% | Colorant | LCW |
| (A) Unipure Black LC989 | Iron Oxides (CL 77499) | 1.5500% | 100.00% | Colorant | LCW |
| (A) Boron Nitride Powder C6058 | Boron Nitride | 1.0000% | 100.00% | Slip Agent | GE Advanced Ceramics |
| (A) Bisabolol Nat. | Bisabolol | 0.1000% | 100.00% | Skin Soothing Agent | BASF |
| (A) Unfermented Green Rooibos Extract | Aspalathus Linearis Leaf Extract | 0.1000% | 100.00% | Antioxidant | Jarchem |
| (B) Mearlmica SVA | Mica (and) Lauroyl Lysine | 20.0000% | 95.50%, 4.50% | Visual Effect | BASF |
| (B) Mearlmica MMCF | Mica | 11.8500% | 100.00% | Visual Effect | BASF |
| (B) Pearl-Glo UVR | Bismuth Oxychloride CL77163 | 18.0000% | 100.00% | Skin Adhesion | BASF |
| (B) Flamenco Satin Gold 260M | Mica (and) Titanium Dioxide (and) Iron Oxides (CL77491) | 6.0000% | 36.00%, 62.00%, 2.00% | Colorant | BASF |
| (B) Flamenco Satin Red 460M | Mica (and) Titanium Dioxide (and) Iron Oxides (CL77491) | 6.0000% | 30.00%, 68.00%, 2.00% | Colorant | BASF |
| (B) Mearlmica MMCF | Mica | 2.0000% | 100.00% | Visual Effect | BASF |

Example 3

The table below provides a list of ingredients for a loose powder mineral foundation having an SPF of 15, and an "Latte" or "medium" shade.

| Trade Name (*phase A or B indicated in brackets) | INCI Name | % Wt | % Comp Breakdown | Function | Manufacturer |
|---|---|---|---|---|---|
| (A) Z-Cote | Zinc Oxide | 12.00% | 100.00% | Sunscreen | BASF |
| (A) Atlas White Titanium Dioxide | Titanium Dioxide | 25.00% | 100.00% | Colorant | LCW |
| (A) Unipure Red LC381 | Iron Oxides (CL 77491) | 1.07% | 100.00% | Colorant | LCW |
| (A) Unipure Yellow LC181 | Iron Oxides (CL 77492) | 5.53% | 100.00% | Colorant | LCW |
| (A) Unipure Black LC989 | Iron Oxides (CL 77499) | 0.44% | 100.00% | Colorant | LCW |
| (A) Boron Nitride Powder C6058 | Boron Nitride | 1.00% | 100.00% | Slip Agent | GE Advanced Ceramics |
| (A) Bisabolol Nat. | Bisabolol | 0.10% | 100.00% | Skin Soothing Agent | BASF |
| (A) Unfermented Green Rooibos Extract | Aspalathus Linearis Leaf Extract | 0.10% | 100.00% | Antioxidant | Jarchem |
| (B) Mearlmica SVA | Mica (and) Lauroyl Lysine | 20.00% | 95.50%, 4.50% | Visual Effect | BASF |
| (B) Mearlmica MMCF | Mica | 10.76% | 100.00% | Visual Effect | BASF |
| (B) Pearl-Glo UVR | Bismuth Oxychloride CL77163 | 10.00% | 100.00% | Skin Adhesion | BASF |
| (B) Flamenco Satin Gold 260M | Mica (and) Titanium Dioxide (and) Iron Oxides (CL77491) | 6.00% | 36.00%, 62.00%, 2.00% | Colorant | BASF |
| (B) Flamenco Satin Red 460M | Mica (and) Titanium Dioxide (and) Iron Oxides (CL77491) | 6.00% | 30.00%, 68.00%, 2.00% | Colorant | BASF |
| (B) Mearlmica MMCF | Mica | 2.00% | 100.00% | Visual Effect | BASF |

Example 4

The table below provides a list of ingredients for a loose powder mineral foundation having an SPF of 15, and an "Light" or "Frost" shade.

The above formulations are prepared by combining all of the phase A ingredients, and mixing for a time, TO=3'+3'+/−30", and at a velocity, V=3600+/−200 g/min, level 3. The mixture is then checked for indispersibles and the color is evaluated (e.g. by comparing to a standard). The Phase B ingredients are then added to the phase A mixture, and the combination is mixed for TO=1'+1'+/−30", at V=3600+/−200 g/min, level 3. The mixture is again checked for indispersibles and color, and the batch is preferably matched to a standard.

| Trade Name (*phase A or B indicated in brackets) | INCI Name | % Wt | % Comp Breakdown | Function | Manufacturer |
|---|---|---|---|---|---|
| (A) Z-Cote | Zinc Oxide | 12.0000% | 100.00% | Sunscreen | BASF |
| (A) Atlas White Titanium Dioxide | Titanium Dioxide | 22.5000% | 100.00% | Colorant | LCW |
| (A) Unipure Red LC381 | Iron Oxides (CL 77491) | 0.5870% | 100.00% | Colorant | LCW |
| (A) Unipure Yellow LC181 | Iron Oxides (CL 77492) | 2.2400% | 100.00% | Colorant | LCW |
| (A) Unipure Black LC989 | Iron Oxides (CL 77499) | 0.430% | 100.00% | Colorant | LCW |
| (A) Boron Nitride Powder C6058 | Boron Nitride | 1.0000% | 100.00% | Slip Agent | GE Advanced Ceramics |
| (A) Bisabolol Nat. | Bisabolol | 0.1000% | 100.00% | Skin Soothing Agent | BASF |
| (A) Unfermented Green Rooibos Extract | Aspalathus Linearis Leaf Extract | 0.1000% | 100.00% | Antioxidant | Jarchem |
| (B) Mearlmica SVA | Mica (and) Lauroyl Lysine | 20.0000% | 95.50%, 4.50% | Visual Effect | BASF |
| (B) Mearlmica MMCF | Mica | 1.4650% | 100.00% | Visual Effect | BASF |
| (B) Pearl-Glo UVR | Bismuth Oxychloride CL77163 | 2.9650% | 100.00% | Skin Adhesion | BASF |
| (B) Flamenco Satin Gold 260M | Mica (and) Titanium Dioxide (and) Iron Oxides (CL77491) | 6.0000% | 36.00%, 62.00%, 2.00% | Colorant | BASF |
| (B) Flamenco Satin Red 460M | Mica (and) Titanium Dioxide (and) Iron Oxides (CL77491) | 6.0000% | 30.00%, 68.00%, 2.00% | Colorant | BASF |
| (B) Mearlmica MMCF | Mica | 2.00% | 100.00% | Visual Effect | BASF |

In closing, it is to be understood that the exemplary embodiments described herein are illustrative of the principles of the present invention. Other modifications that may be employed are within the scope of the invention. Thus, by way of example, but not of limitation, alternative configurations may be utilized in accordance with the teachings herein. Accordingly, the description is illustrative and not meant to be a limitation thereof.

What is claimed:

1. A skin cosmetic method comprising:
   a) providing a facial skin cosmetic, which is adaptable to a range of different skin tones, said cosmetic comprising:
      i) colorants comprising:
         a) special effect pigments consisting essentially of: 1) gold/yellow special effect pigments, and 2) red special effect pigments,
            each of said special effect pigments being present at a concentration of approximately between 2 and 7% by weight of total composition, with a ratio of gold/yellow to red pigment of about between 1:2 and 2:1,
            said special effect pigments have a refractive index range from 2.4 to 2.8, and a d50 particle size of between approximately 6 μm to 300 nm, and
         b) non-special effect colorants comprising iron oxides;
      ii) unfermented green rooibos extract at a concentration of approximately 0.01% to 2% by weight of total composition,
      iii) boron nitride powder at a concentration of approximately 0.1-10% by weight of total composition,
      iv) zinc oxide at a concentration of approximately 9-15% by weight of total composition,
      v) bisabolol at a concentration of approximately at least 0.05% by weight of total composition,
      vi) lauroyl lysine coated mica at a concentration of approximately 15 to 30% by weight of total composition, and
      vii) bismuth oxychloride at a concentration of approximately 5 to 30% by weight of total composition, and
      said composition having an apparent mass tone, wherein said composition is adaptable to a range of at least 6 different skin tones including tones outside said apparent mass tone,
   b) applying said cosmetic to a user's skin, said user having a skin tone within said range of different skin tones.

2. The method of claim 1, said gold special effect pigment having a d50 particle size of approximately 7.9 μm, and said red special effect pigment having a d50 particle size of approximately 6.8 μm.

3. The method of claim 1, said special effect pigments having a mica base with an interference layer comprising titanium dioxide.

4. The method of claim 3, said titanium dioxide layer of said special effect pigments having an optical thickness of approximately 190 nm for the gold pigment, and approximately 260 nm for the red pigment.

5. The method of claim 1, said ratio gold/yellow to red pigments being approximately 1:1.

6. The method of claim 1, said zinc oxide being present at a concentration of approximately 12% by weight of total composition.

7. A cosmetic composition comprising a foundation, cover-up, concealer, or finishing powder, said cosmetic comprising:
   colorants comprising:
      a) special effect pigments consisting essentially of: i) gold or yellow special effect pigments, and ii) red special effect pigments,
      b) non-special effect colorants comprising iron oxides,
      c) unfermented green rooibos extract at a concentration of approximately 0.01% to 2% by weight of total composition, d) boron nitride powder at a concentration of approximately 0.1-10% by weight of total composition, e) zinc oxide at a concentration of approximately 9-15% by weight of total composition, f) bisabolol at a concentration of approximately at least 0.05% by weight of total composition, g) lauroyl lysine coated mica at a concentration of approximately 15 to 30% by weight of total composition, h) bismuth oxychloride at a concentration of approximately 5 to 30% by weight of total composition, and i) mica,
   said composition having an apparent mass tone, wherein said composition is adaptable to a range of at least 6 different skin tones including tones outside said apparent mass tone; and
   a suitable cosmetic medium for application to the skin of a user.

8. The composition of claim 7, each of said special effect pigments being present at a concentration of between about 0.1% to 20% by weight of composition.

9. A skin cosmetic method comprising:
   a) providing a cosmetic comprising a foundation, cover up, concealer, or finishing powder, which is adaptable to a range of different skin tones, said cosmetic comprising:
      i) gold or yellow special effect pigments at a concentration of approximately between 0.1% to 20% by weight of total composition,
      ii) red special effect pigments, at a concentration of approximately between 0.1% to 20% by weight of total composition
      iii) non-special effect colorants comprising iron oxides,
      iii) unfermented green rooibos extract at a concentration of approximately 0.01% to 2% by weight of total composition, iv) boron nitride powder at a concentration of approximately 0.1-10% by weight of total composition, v) zinc oxide at a concentration of approximately 9-15% by weight of total composition, vi) bisabolol at a concentration of approximately at least 0.05% by weight of total composition, vii) lauroyl lysine coated mica at a concentration of approximately 15 to 30% by weight of total composition, viii) bismuth oxychloride at a concentration of approximately 5 to 30% by weight of total composition, and ix) mica,
      said composition having an apparent mass tone, wherein said composition is adaptable to a range of at least 6 different skin tones including tones outside said apparent mass tone; and
   b) applying said composition to the skin of a user having a skin tone within said range of at least 6 different skin tones.

10. The composition of claim 9, said special effect pigments have a refractive index range from 2.4 to 2.8, and a d50 particle size between 6 μm and 300 nm.

* * * * *

UNITED STATES PATENT AND TRADEMARK OFFICE
CERTIFICATE OF CORRECTION

| | | |
|---|---|---|
| PATENT NO. | : 8,252,298 B2 | |
| APPLICATION NO. | : 12/701394 | |
| DATED | : August 28, 2012 | |
| INVENTOR(S) | : Kimber Maderazzo et al. | |

It is certified that error appears in the above-identified patent and that said Letters Patent is hereby corrected as shown below:

On the Title Page, under Related U.S. Application Data add
-- (63) Continuation-in part of International Application No. PCT/US2008/002148, filed February 19, 2010, which claims the benefit of U.S. Patent Application No. 11/899,773 filed September 7, 2007, now abandoned. --

In Column 1, lines 6-18
"This application is related to, and claims priority through earlier filed Provisional Patent Application Ser. No. 61/152, 587, filed on Feb. 13, 2009, which is related to, and claims priority through earlier filed International Patent Application Serial No. US2008/002148, filed on Feb. 19, 2008, which is related to and claims priority through earlier filed U.S. Continuation-in-Part application Ser. No. 11/899,773, filed on Sep. 7, 2007, which is related to, and claims priority through earlier filed U.S. application Ser. No. 111655,420, filed Jan. 19, 2007, all the subject matter of which are herein incorporated by this reference thereto in their entirety for all purposes." should be changed to
-- This patent application is a continuation in part of International Patent Application Serial No. PCT/US2008/002148, filed on February 19, 2008, which claims the benefit of U.S. Patent Application Serial No. 11/899,773, filed on September 7, 2007 (now abandoned); and this application claims the benefit of U.S. Provisional Patent Application Serial No. 61/152,587 filed February 13, 2009, which applications are incorporated in their entirety here by this reference. --

Signed and Sealed this
Sixteenth Day of October, 2012

David J. Kappos
*Director of the United States Patent and Trademark Office*